(12) United States Patent
Gregory et al.

(10) Patent No.: US 9,204,957 B2
(45) Date of Patent: Dec. 8, 2015

(54) SYSTEMS AND METHODS FOR HEMORRHAGE CONTROL AND OR TISSUE REPAIR

(75) Inventors: Kenton W. Gregory, Portland, OR (US); Paul F. Bente, IV, Brentwood, CA (US); Heather Margaret Bryan, San Francisco, CA (US); Jeffrey Yihyuan Lin, Rowland Heights, CA (US); Aileen Nuguid, San Gabriel, CA (US); Daniel Allen Pederson, Winters, CA (US)

(73) Assignee: HEMCON MEDICAL TECHNOLOGIES, INC., Portland, OR (US)

( * ) Notice: Subject to any disclaimer, the term of this patent is extended or adjusted under 35 U.S.C. 154(b) by 190 days.

(21) Appl. No.: 11/084,688

(22) Filed: Mar. 17, 2005

(65) Prior Publication Data

US 2006/0211973 A1 Sep. 21, 2006

(51) Int. Cl.
*A61F 2/04* (2013.01)
*A61F 13/14* (2006.01)
*A61B 17/00* (2006.01)
(Continued)

(52) U.S. Cl.
CPC .................. *A61F 2/04* (2013.01); *A61F 13/148* (2013.01); *A61B 17/00234* (2013.01); *A61B 17/1114* (2013.01); *A61F 2002/044* (2013.01); *A61F 2002/045* (2013.01); *A61F 2013/00463* (2013.01)

(58) Field of Classification Search
CPC ................... A61F 2002/044; A61F 2002/045; A61F 15/005; A61B 1/00082; Y10S 623/902
USPC ......... 623/23.72, 23.64, 23.65; 606/111, 213; 600/115, 116
See application file for complete search history.

(56) References Cited

U.S. PATENT DOCUMENTS 2,610,625 A 9/1952 Sifferd et al.
2,858,830 A 11/1958 Robins
(Continued)

FOREIGN PATENT DOCUMENTS

EP 0353972 2/1990
EP 0477979 9/1991
(Continued)

OTHER PUBLICATIONS

Bendix., "Chemical synthesis of polyactide and its copolymers for medical applications." Polymer Degradation and Stability, vol. 59: 129-135, 1998.

(Continued)

*Primary Examiner* — Diane Yabut
(74) *Attorney, Agent, or Firm* — Miller Nash Graham & Dunn LLP; Chandra E. Eidt

(57) ABSTRACT

A bandage application system of the present for hemorrhage control and/or tissue repair of the gastrointestinal tract, such as the gastrointestinal tract is provided. The system comprises a bandage for hemorrhage control and/or tissue repair of the gastrointestinal tract. It also includes an apparatus for introducing the bandage into a treatment area of the gastrointestinal tract requiring hemorrhage control and/or tissue repair, and for removing the apparatus from the treatment area without displacing the bandage from being adhered to the treatment area, and without damaging the gastrointestinal tract. Furthermore, it also has a device for adhering the bandage to the treatment area.

28 Claims, 2 Drawing Sheets

(51) Int. Cl.
*A61B 17/11* (2006.01)
*A61F 13/00* (2006.01)

(56) References Cited

U.S. PATENT DOCUMENTS

| | | |
|---|---|---|
| 2,923,664 A | 2/1960 | Cook et al. |
| 3,551,556 A | 12/1970 | Kliment et al. |
| 3,632,754 A | 1/1972 | Belassa |
| 3,800,792 A | 4/1974 | McKnight et al. |
| 3,801,675 A | 4/1974 | Russell |
| 3,849,238 A | 11/1974 | Gould et al. |
| 3,902,497 A | 9/1975 | Casey |
| 3,911,116 A | 10/1975 | Balassa |
| 3,954,493 A | 5/1976 | Battista et al. |
| 3,977,406 A | 8/1976 | Roth |
| 4,040,884 A | 8/1977 | Roth |
| 4,056,103 A | 11/1977 | Kaczmarzyk et al. |
| 4,068,757 A | 1/1978 | Casey |
| 4,094,743 A | 6/1978 | Leuba |
| 4,195,175 A | 3/1980 | Peniston et al. |
| 4,292,972 A | 10/1981 | Pawelchak et al. |
| 4,373,519 A | 2/1983 | Errede et al. |
| 4,394,373 A | 7/1983 | Malette et al. |
| 4,452,785 A | 6/1984 | Malette et al. |
| 4,460,642 A | 7/1984 | Errede et al. |
| 4,501,835 A | 2/1985 | Berke |
| 4,524,064 A | 6/1985 | Nambu |
| 4,532,134 A | 7/1985 | Malette et al. |
| 4,533,326 A | 8/1985 | Anthony |
| 4,541,426 A | 9/1985 | Webster |
| 4,599,209 A | 7/1986 | Dautzenberg et al. |
| 4,651,725 A | 3/1987 | Kifune et al. |
| 4,684,370 A | 8/1987 | Barrett |
| 4,699,135 A | 10/1987 | Motosugi et al. |
| 4,759,348 A | 7/1988 | Cawood |
| 4,772,419 A | 9/1988 | Malson et al. |
| 4,833,237 A | 5/1989 | Kawamura et al. |
| 4,948,540 A | 8/1990 | Nigam |
| 4,952,618 A | 8/1990 | Olsen |
| 4,956,350 A | 9/1990 | Mosbey |
| 4,958,011 A | 9/1990 | Bade |
| 4,960,413 A | 10/1990 | Sagar et al. |
| 4,973,493 A | 11/1990 | Guire |
| 4,977,892 A | 12/1990 | Ewall |
| 5,006,071 A | 4/1991 | Carter |
| 5,024,841 A | 6/1991 | Chu et al. |
| 5,062,418 A | 11/1991 | Dyer et al. |
| 5,110,604 A | 5/1992 | Chu et al. |
| 5,116,824 A | 5/1992 | Miyata et al. |
| 5,154,928 A | 10/1992 | Andrews |
| 5,206,028 A | 4/1993 | Li |
| 5,254,301 A | 10/1993 | Sessions et al. |
| 5,300,494 A | 4/1994 | Brode, II et al. |
| 5,376,376 A | 12/1994 | Li |
| 5,378,472 A | 1/1995 | Muzzarelli |
| 5,420,197 A | 5/1995 | Lorenz et al. |
| 5,454,719 A | 10/1995 | Hamblen |
| 5,525,710 A | 6/1996 | Unger et al. |
| 5,571,181 A | 11/1996 | Li |
| 5,597,581 A | 1/1997 | Kaessmann et al. |
| 5,643,596 A | 7/1997 | Pruss et al. |
| 5,700,476 A | 12/1997 | Rosenthal et al. |
| 5,738,860 A | 4/1998 | Schonfeldt |
| 5,756,111 A | 5/1998 | Yoshikawa et al. |
| 5,765,682 A | 6/1998 | Bley et al. |
| 5,797,960 A * | 8/1998 | Stevens et al. ............... 606/213 |
| 5,821,271 A | 10/1998 | Roenigk |
| 5,827,265 A | 10/1998 | Glinsky et al. |
| 5,836,970 A | 11/1998 | Pandit |
| 5,840,777 A | 11/1998 | Eagles et al. |
| 5,858,292 A | 1/1999 | Dragoo et al. |
| 5,858,350 A | 1/1999 | Vournakis et al. |
| 5,952,618 A | 9/1999 | Deslauriers |
| 5,961,478 A | 10/1999 | Timmermans |
| 6,042,877 A | 3/2000 | Lyon et al. |
| 6,054,122 A | 4/2000 | MacPhee et al. |
| 6,103,369 A | 8/2000 | Lucast et al. |
| 6,124,273 A | 9/2000 | Drohan et al. |
| 6,156,330 A | 12/2000 | Tsukada et al. |
| 6,162,241 A | 12/2000 | Coury et al. |
| 6,225,521 B1 | 5/2001 | Gueret |
| 6,270,515 B1 * | 8/2001 | Linden et al. ................. 606/213 |
| 6,406,712 B1 | 6/2002 | Rolf |
| 6,448,462 B2 | 9/2002 | Groitzsch et al. |
| 6,454,787 B1 | 9/2002 | Maddalo et al. |
| 6,485,667 B1 | 11/2002 | Tan |
| 6,486,285 B2 | 11/2002 | Fujita |
| 6,548,081 B2 | 4/2003 | Sadozai et al. |
| 6,548,569 B1 | 4/2003 | Williams et al. |
| 6,552,244 B1 | 4/2003 | Jacques et al. |
| 6,565,878 B2 | 5/2003 | Schoenfedlt et al. |
| 6,566,577 B1 | 5/2003 | Addison et al. |
| 6,599,891 B2 | 7/2003 | North et al. |
| 6,693,180 B2 | 2/2004 | Lee et al. |
| 6,726,712 B1 | 4/2004 | Raeder-Devens et al. |
| 6,855,860 B2 | 2/2005 | Ruszczak et al. |
| 6,863,924 B2 | 3/2005 | Ranganathan et al. |
| 6,864,245 B2 | 3/2005 | Vournakis et al. |
| 6,992,233 B2 | 1/2006 | Drake et al. |
| 7,019,191 B2 | 3/2006 | Looney et al. |
| 7,371,403 B2 | 5/2008 | McCarthy et al. |
| 7,402,172 B2 | 7/2008 | Chin et al. |
| 7,482,503 B2 | 1/2009 | Gregory et al. |
| 7,546,812 B2 | 6/2009 | Eastin et al. |
| 7,637,934 B2 | 12/2009 | Mangiardi et al. |
| 7,671,102 B2 | 3/2010 | Gaserod et al. |
| 7,820,872 B2 | 10/2010 | Gregory et al. |
| 7,897,832 B2 | 3/2011 | McAdams et al. |
| 8,063,265 B2 | 11/2011 | Beck et al. |
| 2001/0045177 A1 | 11/2001 | Harvey et al. |
| 2002/0035391 A1 * | 3/2002 | Mikus et al. ................. 623/1.11 |
| 2002/0161376 A1 | 10/2002 | Barry et al. |
| 2005/0036955 A1 | 2/2005 | DeGould |
| 2005/0123581 A1 | 6/2005 | Ringeisen et al. |
| 2005/0137512 A1 | 6/2005 | Campbell et al. |
| 2005/0143817 A1 * | 6/2005 | Hunter et al. ............... 623/11.11 |
| 2005/0147656 A1 | 7/2005 | McCarthy et al. |
| 2005/0234508 A1 * | 10/2005 | Cummins et al. ............. 606/213 |
| 2005/0240137 A1 * | 10/2005 | Zhu et al. ...................... 602/56 |
| 2006/0004314 A1 | 1/2006 | McCarthy et al. |
| 2006/0008419 A1 | 1/2006 | Hissink et al. |
| 2006/0079957 A1 * | 4/2006 | Chin et al. .................... 623/1.42 |
| 2006/0083710 A1 | 4/2006 | Joerger et al. |
| 2006/0184224 A1 | 8/2006 | Angel |
| 2006/0211973 A1 | 9/2006 | Gregory et al. |
| 2007/0021703 A1 | 1/2007 | McCarthy |
| 2007/0066920 A1 | 3/2007 | Hopman et al. |
| 2007/0083137 A1 | 4/2007 | Hopman et al. |
| 2007/0237811 A1 | 10/2007 | Scherr |
| 2007/0255194 A1 | 11/2007 | Gudnason et al. |
| 2007/0255243 A1 | 11/2007 | Kaun et al. |
| 2007/0276308 A1 | 11/2007 | Huey et al. |
| 2008/0132990 A1 | 6/2008 | Richardson |
| 2008/0147019 A1 | 6/2008 | Song et al. |
| 2008/0241229 A1 | 10/2008 | Li et al. |

FOREIGN PATENT DOCUMENTS

| | | |
|---|---|---|
| EP | 0643963 | 3/1995 |
| EP | 1462123 | 9/2004 |
| JP | 60-142927 | 7/1985 |
| JP | 62-039506 | 2/1987 |
| JP | 63-090507 | 4/1988 |
| JP | 07-116241 | 5/1995 |
| JP | 11-342153 | 12/1999 |
| JP | 2002-233542 | 8/2002 |
| WO | WO 95/05794 | 3/1995 |
| WO | WO 99/02587 | 1/1999 |
| WO | WO 00/56256 | 9/2000 |
| WO | WO 2002/102276 | 12/2002 |
| WO | WO 03/047643 | 6/2003 |
| WO | WO 03/079946 | 10/2003 |
| WO | WO 03/092756 | 11/2003 |
| WO | WO 2004/047695 | 6/2004 |

(56) References Cited

FOREIGN PATENT DOCUMENTS

| WO | WO 2004/060412 | 7/2004 |
|---|---|---|
| WO | WO 2005062880 | 7/2005 |
| WO | WO 2006049463 | 5/2006 |
| WO | WO 2006071649 | 7/2006 |
| WO | WO 2006/079822 | 8/2006 |
| WO | WO 2007009050 | 1/2007 |
| WO | WO 2007056066 | 5/2007 |
| WO | WO 2007074327 | 7/2007 |
| WO | WO 2008033462 | 3/2008 |
| WO | WO 2008036225 | 3/2008 |

OTHER PUBLICATIONS

Schoof et al., "Control of Pore Structure and Size in Freeze-Dried Collagen Sponges." Journal of Biomedical Material Research, vol. 58: 352-357, 2001.
Wu et al., "Development of In Vitro Adhesion Test for Chitosan Bandages." Society for Biomaterials 30th Annual Meeting Transactions, 2005, 1pg.
Database WPI, Week 200783 Thomson Scientific, London GB, AN 2008-M34232, XP002695569 & CN 101138648, Mar. 12, 2008.
Allan et al., "Biomedical Applications of Chitin and Chitosan." Chitin, Chitosan, and Related Enzymes—Accademic Press, Inc.: 119-133, 1984.
Anema et al., "Potential Uses of Absorbable Fibrin Adhesive Bandage for Genitourinary Trauma." World Journal of Surgery, vol. 25: 1573-1577, 2001.
Bégin et al., "Antimicrobial films produced from chitosan." International Journal of Biological Macromolecules, vol. 26: 63-67, 1999.
Belman et al., "From the Battlefield to the Street." Per declaration submitted in U.S. Appl. No. 10/480,827, dated Dec. 17, 2007, poster presentation was made at the ATACCC Conference, Aug. 2006.
Chan et al., "Comparision of Poly-N-acetyl Glucosamine (P-GlcNAc) with Absorbable Collagen (Actifoam), and Fibrin Sealant (Bolheal) for Achieving Hemostasis in a Swine Model of Splenic Hemorrhage." The Journal of Trauma: 454-458, 2000.
CNN Transcript—3pp., Jun. 8, 2006.
Cole et al., "A pilot study evaluating the efficacy of a fully acetylated poly-N-acetyl glucosamine membrane formulation as a topical hemostatic agent," Surgery, vol. 126, No. 3: 510-517, 1999.
HemCon Manufacturing Materials. Per declaration submitted in U.S. Appl. No. 10/480,827, dated Dec. 17, 2007, materials were submitted as supporting evidence for declaration.
Horesh et al., "Pre-hospital use of the HemCon bandage." Per declaration submitted in U.S. Appl. No. 10/480,827, dated Dec. 17, 2007, poster presentation was made at the WCDEM Conference, May 2007.
Kiley, Kevin, "Department of the Army memo." Jul. 20, 2005.
Kumar, Ravi, "Chitin and chitosan fibres: A review." Bulletin of Material Science: vol. 22, No. 5: 905-915, Aug. 1999.
Luo et al., "The role of poly(ethylene gycol) in the formation of silver nanoparticles." Journal of Colloid and Interface Science, vol. 288: 444-448, 2005.
Malette et al., "Chitosan: A New Hemostatic," The Annals of Thoratic Surgery, vol. 36, No. 1: 55-58, Jul. 1983.
Martin et al., "Medical applications of poly-4-hydroxybutyrate: a strong flexible absorbable biomaterial." Biochemical Engineering Journal, vol. 16: 97-105, 2003.
Mi et al., "Fabrication and characterization of a sponge-like asymmetric chitosan membrane as a wound dressing." Biomaterials, vol. 22: 165-173, 2001.
Moody, Robin J., "HemCon bandage stakes claim to soldier's kit bag." Portland Business Journal, Nov. 4, 2005.
Ohshima et al., "Clinical Application of Chitin Non-Woven Fabric as Wound Dressing." European Journal of Plastic Surgery, vol. 10: 66-69, 1987.
Ohshima et al., "Clinical application of new chitin non-woven fabric and new chitin sponge sheet as wound dressing." European Journal of Plastic Surgery, vol. 14: 207-211, 1991.
Olsen et al., "Biomedical Applications of Chitin and its Derivatives." Chitin and Chitosan: Proceedings of the 4th International Conference on Chitin and Chitosan, 813-829, 1988.
Park et al., "Platelet derived growth factor releasing chitosan sponge for periodontal bone regeneration." Biomaterials, vol. 21: 153-159, 2000.
Percot et al., "Optimization of Chitin Extraction from Shrimp Shells." Biomacromolecules, vol. 4: 12-18, 2003.
Pusateri et al., "Advanced Hemostatic Dressing Development Program: Animal Model Selection Criteria and Results of a Study of Nine Hemostatic Dressings in a Model of Severe Large Venous Hemorrhage and Hepatic Injury in Swine." The Journal of Trauma, vol. 55: 518-526, 2003.
Sandford, Paul A., "Chitosan: Commercial Uses and Potential Applications." Chitin and Chitosan: Proceedings from the 4th International Conference on Chitin and Chitosan, 51-69, 1988.
Sandford et al., "Biomedical Applications of High-Purity Chitosan." Water-Soluble Polymers: Chapter 28: 430-445, 1991.
Sandford, Paul A., "Biomedical Applications of New Forms of Chitin/Chitosan." Chitin Derivatives in Life Science, 12pp., 1992.
Siekman, Philip, "A Shrimp Bandage?" Fortune Small Business, pp. 67-68, 2006.
Sondeen et al., "Comparison of 10 Different Hemostatic Dressings in an Aortic Injury." The Journal of Truma, vol. 54, No. 2: 280-285, 2003.
Wedmore et al., "A Special Report on the Chitosan-based Hemostatic Dressing: Experience in Current Combat Operations." The Journal of Trauma, vol. 60: 655-658, 2006.
Wilson, J.R., "The Army's Greatest Inventions." U.S. Army Materiel Command, pp. 30-37, 2005.

\* cited by examiner

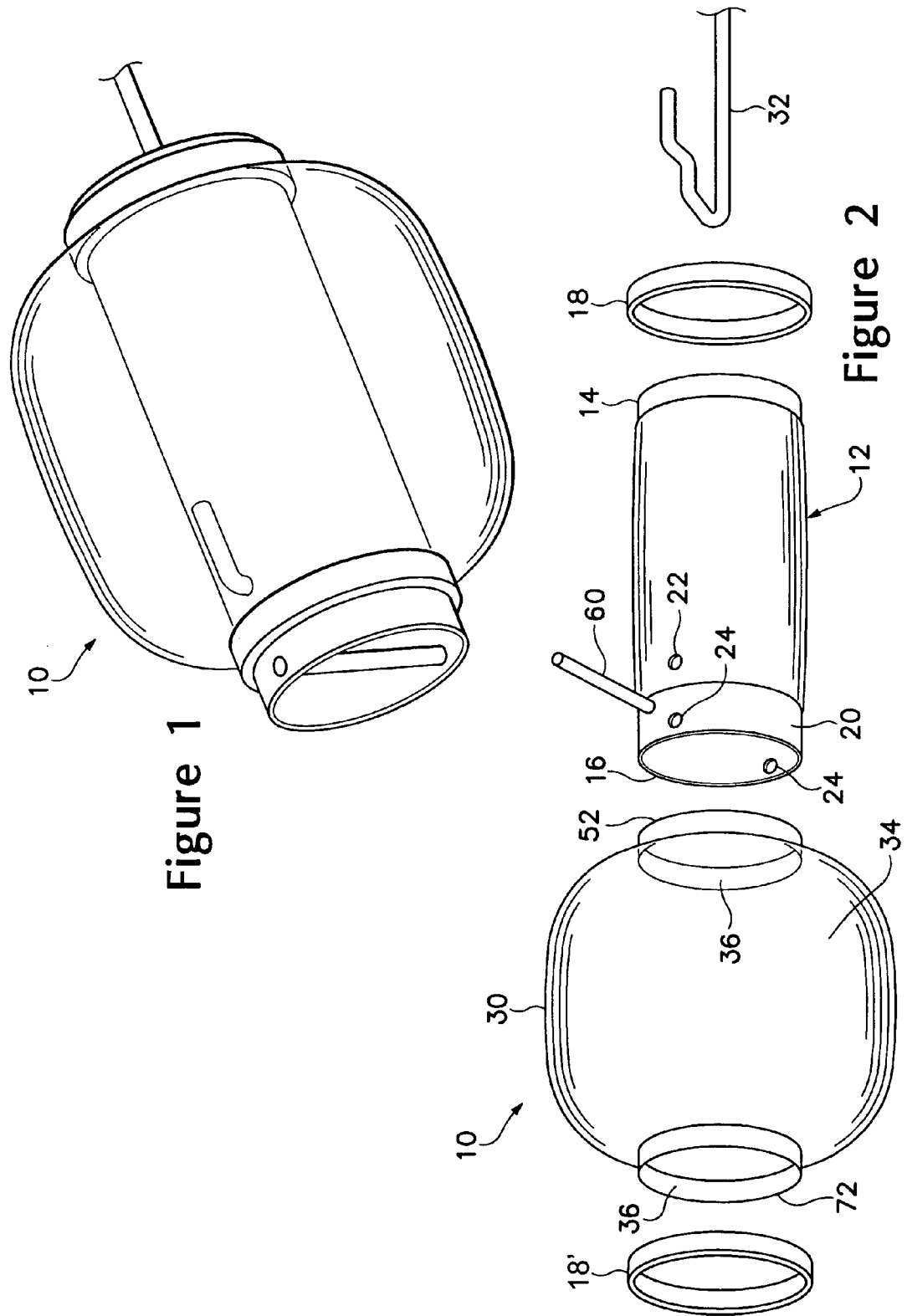

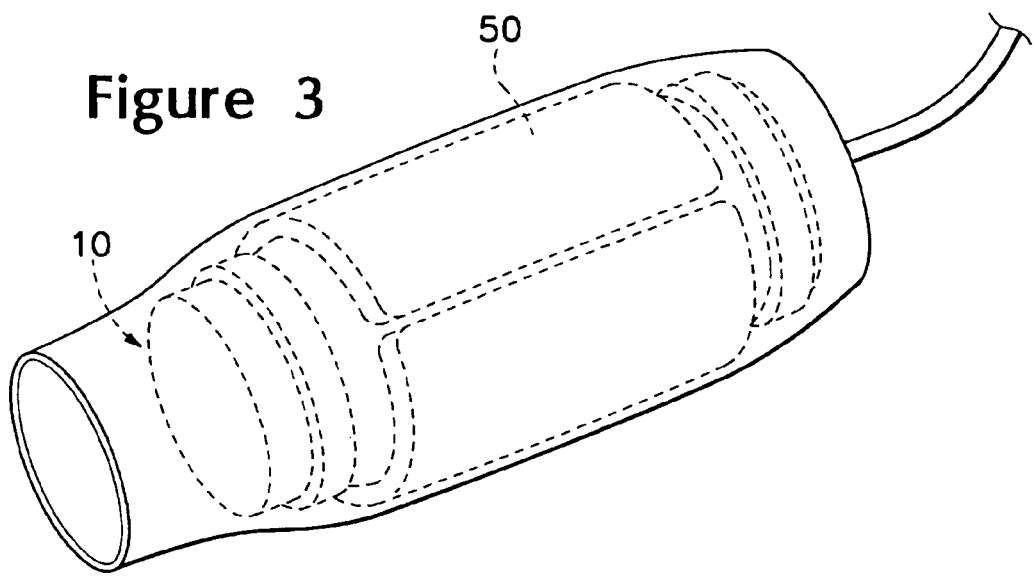
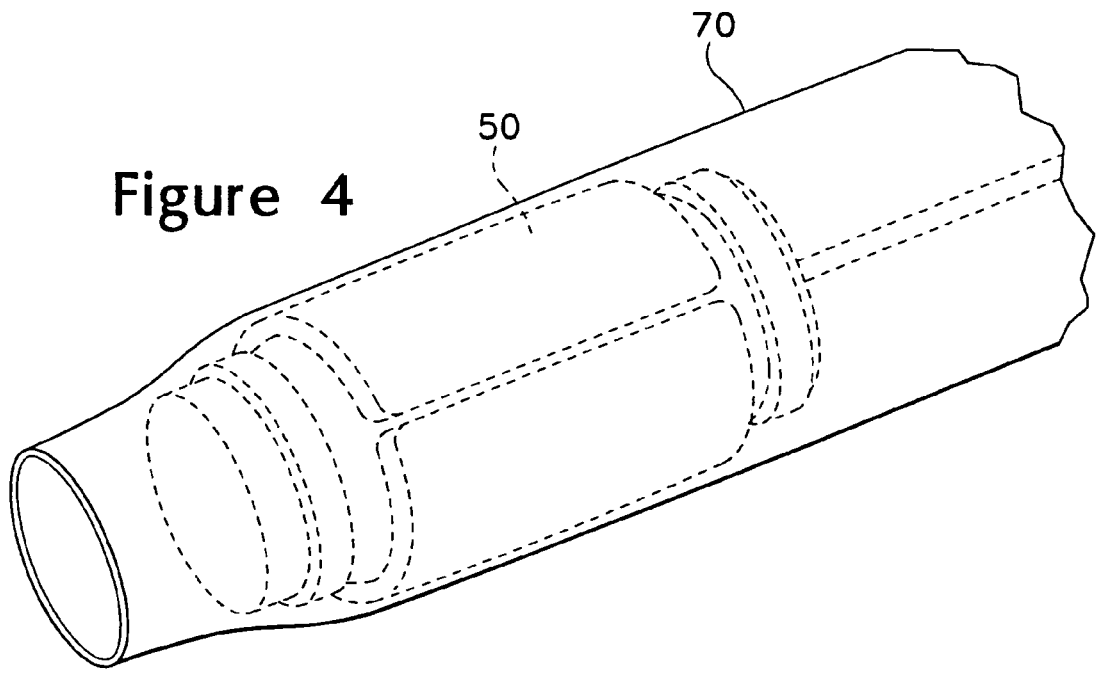

SYSTEMS AND METHODS FOR HEMORRHAGE CONTROL AND OR TISSUE REPAIR

GOVERNMENT LICENSE RIGHTS

This invention was made with government support from the United States Army Medical Research and Materiel Command, under United States Army Medical Research Acquisition Activity cooperative agreement no. DAMD17-01-20030. The United States government has certain rights in this invention.

BACKGROUND OF THE INVENTION

This invention relates to systems and methods for hemorrhage control and/or tissue repair of the gastrointestinal tract, and more particularly, an application system and method for effectively and efficiently bandaging a treatment area of an esophagus, stomach, duodenum, small intestine and large intestine or other structures in the gastrointestinal tract requiring hemorrhage control and/or tissue repair without damaging the gastrointestinal tract.

The esophagus is the muscular, membranous tube, through which food is passed, which extends from the pharynx to the stomach. Hemorrhage control and tissue repair are difficult to affect within the esophageal tract.

The esophagus can be severely injured resulting in hemorrhage and tissue injury through penetrating trauma or from forceful emesis causing tears termed Mallory Weiss Tears. Ulceration of the esophagus and other gastrointestinal tissues can have hemorrhage and tissue injury. The esophagus is also injured and perforated by physicians using endoscopes. Surgical resections of esophageal cancers and other lesions requiring end to end and other anastomosis can hemorrhage and have tissue injury. In cases with perforations or surgical resections of the esophagus, frequently the most serious, life threatening consequences are caused by leaks of esophageal contents into the mediastinum resulting in debilitating and life threatening infection due to lack of adequate sealing of the esophageal injury.

Esophageal varices are dilated veins of the portal systemic system which pass through the distal end of the esophagus where it meets with the lesser curvature of the stomach. These veins dilate from a diameter of a few millimeters to a diameter of up to 1 cm due to an increase in blood pressure within them, which pushes against their thin, elastic walls. This portal hypertension is a consequence of the blockage in blood flow further down the path of the portal vein at the liver when fibrosis (scar tissue) is present due to cirrhosis.

When the blood through the portal vein cannot follow its usual path through the liver, it is forced back up the vein in the direction from which it came. Because the portal vein is not constructed to withstand such strong forces, it tends to balloon out at sites of vessel weakness, such as at the base of the esophagus where the vein passes very close to the surface, causing what is clinically known as varices. Esophageal varices are a subject of much concern among the medical community due to the high rate of occurrence and severe complications of the condition. Additionally, of the incidents of esophageal varices, 50% of them will be so severe that the vein will rupture into the esophagus resulting in critical bleeding situations. Patients presenting with an initial case of bleeding esophageal varices have a 40-70% fatality rate, and recurrent bleeding is typical.

Currently there are few effective acute treatment options for patients with bleeding esophageal varices. Ideally, a treatment would be as non-invasive as possible, would not cause any side-effects, would be effective for all cases presented, and would allow for the restoration of the patient's daily lifestyle soon afterward. Unfortunately none of the treatments currently available offer all of these characteristics.

Two common treatments for esophageal varices involve the use of an endoscope to deploy a device at the bleeding site to stop the bleeding. The endoscope is a tool used in most gastrointestinal procedures. It is often used for investigation and diagnosis of upper and lower GI problems. The standard endoscope is a long tubular device. It has a control held by the doctor that manipulates the tip, which is inserted down the patient's esophagus. The endoscope has its own optics system, which is transmitted to a monitor and possible video sampling or recording system. Down the center of the endoscope is a 4 mm hole. This hole is used to insert balloons, forceps or other surgical devices to perform whatever operation is necessary in the GI tract.

One of these devices places a rubber band securely around the opening of the bleeding varix, which simply closes off the injury to the harsh environment of the gastrointestinal (GI) tract with the expectation that it will eventually heal over. However, this method of treatment is only an option for bleeding varices that are relatively small, whereas most problematic varices are often very large. The other endoscopic method of treating acute bleeding in the esophagus utilizes a balloon apparatus which is extended by a wire down the esophagus, past the esophageal-stomach junction and into the upper stomach. It is then blown-up and pulled upwards toward the esophagus. This motion applies pressure to the esophagus at the esophageal-stomach junction, which acts to stop or slow down bleeding from the ruptured varices. Unfortunately, this method is not very effective, and at times physicians find it necessary to assist the process by pouring ice water down the esophagus. Ultimately, this procedure is ineffective against large bleeds, and is only a very temporary solution as it prevents the passage of food into the stomach.

The most extreme method of treating esophageal varices involves the insertion of a transjugular intrahepatic Porto systemic shunt (TIPS) into the hepatic vein in an effort to reduce portal venous pressure. Unfortunately the TIPS procedure is a highly invasive surgery. In addition, it will not cure the immediate problem of bleeding in the esophagus.

Therefore, a need exists for effectively and efficiently controlling esophageal hemorrhaging and/or repairing esophageal or other gastrointestinal tissues. Similarly, such devices could be deployed in the urologic tracts such as the urethra using endoscopic techniques or in the bronchus using bronchoscopes to treat bleeding, perforations, fistulas or other lesions. The ability to deploy a dressing that can stop hemorrhage and seal the lesion, as well as create an antimicrobial barrier, offers great promise to substantially reduce morbidity as a result of these injuries that is poorly addressed by present endoscopic and surgical technologies and techniques. The potential to deliver dressings that clot and seal these lesions rapidly and safely using conventional endoscopes would be of great benefit.

SUMMARY OF THE INVENTION

A bandage application system of the present for hemorrhage control and/or tissue repair of the gastrointestinal tract, such as the esophagus, stomach, duodenum, small intestine and large intestine, can be provided which meets the above-described existing needs. The system comprises a bandage for hemorrhage control and/or tissue repair of the gastrointestinal tract. It also includes an apparatus for introducing the bandage into a treatment area of the gastrointestinal tract requiring hemorrhage control and/or tissue repair, and for removing the apparatus from the treatment area without displacing the bandage from being adhered to the treatment area, and without damaging the gastrointestinal tract. Furthermore, it also has a device for adhering the bandage to the treatment area.

Preferably, the bandage application system is non-invasive. Thus, the system is preferably constructed to be employed conjunction with an endoscopic device. Furthermore, the bandage application system can be introduced into a treatment area of the esophagus under video or fluoroscopic guidance.

The bandage application system can be designed to adhere the bandage to the treatment area by applying pressure to the bandage against the esophagus. More specifically, the bandage application system can be expanded for applying pressure to move the bandage against the esophagus for a period of time sufficient to adhere the bandage to the esophagus.

Furthermore, the bandage application system can be expanded using a gas for applying the pressure to move the bandage against the esophagus for a period of time sufficient to adhere the bandage to the esophagus. Thus, the system can include an expandable member which is expanded by applying the pressure, typically employing air or fluid as the expansion medium, to move the bandage against the esophagus for a period of time sufficient to adhere the bandage to the esophagus. The bandage application system can include a tubular sleeve on which is mounted the expandable member.

The bandage can be formed into a generally substantially tubular shape to encompass all sides of the esophagus. The bandage preferably comprises a chitosan bandage. Preferably, the bandage further includes a protective barrier joined to the bandage so that the bandage does not adhere to the bandage application system or to the esophagus en route to the treatment area. An outer sheath can also be disposed about the bandage to protect the bandage from the wet environment of the esophagus when introducing the bandage into the treatment area.

In one embodiment the treatment includes application of the endoscopic chitosan bandage delivery system to a bleeding or ulcerous lesion in the esophagus, stomach, duodenum, small or large intestine. In one embodiment, tissue repair comprises surgical anastomosis of the esophagus, stomach, duodenum, small intestine and large intestine. In another embodiment, hemorrhage control and/or tissue repair comprises treating bleeding or other wounds in the transurethral prostatectomy. In still another embodiment, hemorrhage control and/or tissue repair comprises treating bronchial bleeding, fistulas or other lesions using a bronchoscope.

The bandage of the present invention can include drugs for additional pharmacologic treatment effects. Preferably, these drugs can comprise anticancer drugs, anti inflammatory drugs, anti-ulcerative colitis drugs, anti-Crohns disease drugs, coagulants, antibiotics, and muscle relaxants.

The system of preferably includes a bandage which is in the shape of a patch. Furthermore, a protective covering can be provided which is removable from the bandage. In one form of the invention, the bandage is comprised of chitosan and at least one additional component. Preferably, the bandage is comprised of chitosan acetate. As for the additional components, they preferably comprise biocompatible synthetic polymer or natural protein coatings, and the biocompatible protein coatings preferably comprise elastin or collagen or other matrix proteins.

The bandage can be used to treat an ulceration or burn. It can also be used to treat an infection such as candidiassis, a viral inflammation or a bacterial infection, or to treat and seal a perforation or fistula or leaking anastomosis.

The system of this invention can be configured so that the tubular sleeve is expanded from a location outside the body. And, the device for adhering the bandage to the treatment area can include a guidewire system on which is mounted the expandable member. Moreover, the device for adhering the bandage to the treatment area can include an expandable nitinol tube on which is mounted said expandable member.

DESCRIPTION OF THE DRAWINGS

FIG. 1 is a perspective view of a preferred system of the present invention.

FIG. 2 is an exploded perspective view of the system of FIG. 1.

FIG. 3 is perspective view of the system of FIG. 1 having a bandage wrapped around the system.

FIG. 4 is perspective view of the system of FIG. 3 having a protective sheath wrapped around the bandage.

DETAILED DESCRIPTION OF PREFERRED EMBODIMENT

Referring to FIGS. 1 and 2, the system 10 of the present invention is compatible with currently available endoscopes. Current available endoscopes (not shown) have optics wired inside of them so that the physician can view the area at the tip of the endoscope on a large monitor. This will aid in quick employment of the system 10 because medical facilities would not need to purchase new, costly endoscopic equipment. Permanent alterations to existing endoscopes would narrow the range of usage of those altered endoscopes. Therefore, the system should not require permanent attachment or alterations to endoscopes which are used to deploy it. To best meet this objective, the system should be detachable after use.

It is important to the success of the system 10 that it be able to accurately deliver the bandage to the treatment used. Accurate delivery typically involves the application of one or more bandages such that the entire treatment area is covered. The system of this invention is designed for reproducible accuracy.

The speed of effectual application of a bandage 50 (see FIG. 3) after diagnosis of the injury bleeding in the treatment area using the system 10 is important. The time required to load the bandage 50 onto the system 10, deploy the bandage 50, and to introduce additional bandages 50 to the treatment area (if needed) is a preferred design feature.

Viewing the affected area is important for the proper placement of the bandage over the injury. Therefore the device should allow for the maximum viewing capability during diagnosis and treatment (bandage application). If the device blocks the field of view, it would be less favorable than one that does not block any part of the viewing angle. This could happen if viewing depends upon the endoscope's internal optics and the device extends beyond the tip of the endoscope. The device should provide feedback to the user (the physician) in such a way that assures the user of proper deployment of the system 10 and accurate application of the bandage. This should involve visualization of the properly adhered bandage after application.

Oregon Medical Laser Center of Portland, Oreg., and its licensee, Hemcon, have developed a bandage that can staunch the flow of life-threatening bleeding. PCT patent application (WO 02/102276 A3) covering such a wound dressing was published on Dec. 27, 2002, and is incorporated herein in it's entirety by reference. This bandage was designed for use on the battlefield, and has been experimentally shown in a porcine model to prevent fatality in 100% of cases in which the aorta was lesioned, as compared to 40% when only gauze and pressure were used. Because the bandage is highly effective, it has been FDA approved and has already been in use to save lives by the U.S. Armed Forces.

A key component of the bandage is chitosan, which is a deacylated derivative of the polysaccharide chitin. Chitosan has a positive charge, and thus attracts and binds red blood cells and platelets, which have a negative charge and are the major catalysts for thrombosis. Also, the positive charge imparts strong muco-adhesive properties to the chitosan bandage. Therefore, the bandage has dual functionality: (a) it adheres to the injured surface, protecting it from harsh external conditions and lessening the amount of blood loss, and (b) it prevents continued bleeding by creating an active clotting surface and seals the injured tissues to stop bleeding, stabilize the wound, and creates an antimicrobial surface.

In addition to all of the useful anti-hemorrhagic properties of chitosan, it is also non-immunogenic and has antimicrobial or antibiotic properties. Thus, the chitosan bandage not only works efficiently to stop bleeding, but also helps to seal wounds. Additionally, a polymeric or protein material, preferably in the form of a fine Vicryl or Dexon mesh or the like, or matrix proteins such as collagen or elastin which may also have other important physiologic effects, serves to provide structure for the chitosan without adding unwanted thickness or inhibiting range of movement that is a non-sticking surface to prevent chitosan from sticking to the delivery device as well as sticking to other surface that adhesion is not desired.

As shown in FIG. 3, the bandage 50 is able to maintain an imposed cylindrical shape and stay wrapped around the system 10. The ability of the bandage to stay wrapped around the system was tested in both an inflated and deflated condition. In the deflated scenario, the bandage wrapped securely around the outside of the system and did not fall off when tilted in several directions. As the system was slowly inflated, the bandage diameter increased along with the increased size of the system. However, the bandage maintained the position wrapped around the outside of the inflated system.

The bandage should have an appropriate thickness and flexibility to be effective in adhering to the treatment area and for hemorrhage control and/or tissue repair. Esophageal damage can often be present around the entire circumference of the esophagus, so it must be possible to cover this entire area. If one bandage is not sufficient to do so, then the application of multiple bandages may be possible. The bandage also must be non-toxic because it will be positioned in the body and, after application, the patient will eventually process the bandage through the digestive system.

The bandage's tubular shape is designed to encompass all sides of the esophagus wall. It may also be compact so that there is sufficient space which will allow more flexibility in the design of the deployment device. Depending on the design of the system, the bandage might need a protective barrier so that it will not stick to the device or the sides of the esophagus en route to the affected area. The bandage should preferably substantially adhere within about 2-5 minutes of applied pressure.

The system 10 will deliver the bandage down the esophagus and maintain the bandage's position on the system. The system will provide protection from moisture of the esophageal wall during the delivery. After reaching the affected treatment area, the system will transfer the bandage from the endoscope or guide wire to the treatment area. The system, will deploy the bandage and then maintain position and apply pressure after the bandage is deployed. The bandage will adhere to the wound and stop bleeding, and the system will provide imaging of the treatment area.

As seen in FIGS. 1 and 2, the backbone of the preferred system 10 is a long thin walled tubular sleeve 12, more preferably a polymeric tube. The sleeve 12 can be formed of a long thin walled piece of polymeric material such as nylon or DELRIN® (which is an acetal polymer manufactured by Dupont). The preferred sleeve 12 is designed to slide easily over the outer diameter of the endoscope tip. The ends 14, 16 of the sleeve preferably have slightly smaller outer diameters, more preferably identified as a locking ring recess. This allows locking rings 18 to fit tightly over the ends 14, 16 of the sleeve and remain in a fixed position.

A small hole 22 can be bored close to the edge of the sleeve to allow for the attachment of an inflation tube. Typically, the snug fit of the sleeve over the endoscope tip does not leave room for the inflation tube to run along space between the sleeve and the endoscope. Therefore, the length from the inflation hole to the nearest edge would extend out beyond the tip of the endoscope. To minimize the sleeve's extension beyond the endoscope, the inflation hole was bored as close to the edge as possible. Two small holes 24 directly across from one another on the front-end locking ring recess to allow for the insertion of a positioning wire 60.

Locking rings 18, 18' are preferably used to attach the edges 14, 16 of the sleeve 12 and to create an airtight seal. The locking rings 18, 18' are preferably formed of a polymeric material such as nylon or DELRIN®. The edges 14, 16 of the rings 18 are preferably beveled to aid in sliding them on the sleeve 12. The ID of the rings 18, 18' is preferably slightly larger than the sleeve recess OD, to account for the thickness of the expandable sleeve 30. The rings 18, 18' perform a locking function due to their tight fit over the expandable sleeve 30. However, the rings 18, 18' are not permanently attached and can be removed to replace the expandable sleeve 30. The length of the rings 18, 18' are preferably shorter than the length of the front locking ring recess 20 to allow for the insertion of positioning wire 60 on the locking ring recess 20 as well.

The dimension of the front locking ring 18 preferably differs from that of the back locking ring 18'. The front locking ring 18 can be thin and, when secured on the sleeve 12, the OD of the locking ring 18 is similar to the OD of the sleeve 12. After deploying the bandage 50, the system 10 must be pulled back up the esophagus, during which the front locking ring 18 must pass by the adhered bandage. Limiting the size of the front locking ring 18 allows the front locking ring 18 to smoothly pass by the bandage, whereas a protruding ring might get caught on the edge of the bandage. The back locking ring 18' is generally relatively thick. The thickness of the back locking ring 18' serves to prevent the bandage from sliding backwards up the sleeve 12.

The sleeve 12 can be molded using an injection molding technique. Its composition, if possible should match that of the expandable sleeve 30 so that they can, alternatively, be bonded together instead of being held in place by the locking rings 18, 18'. Typically, bonding is strongest between similar materials. The sleeve 12 should have a small bending radius without restricting flow, and should be compatible with the final choice of materials for the sleeve 12. Preferably, a polymeric material such as low udometer polyester (PET) can be employed. A PET expandable sleeve 30 can allow for significantly higher pressures to press the bandage against the wall of the esophagus.

A guide wire with a clip (not shown) can direct the bandage down the esophagus along the side of the endoscope or a tube of fiber optics. The guide wire will extend from the wounded area in the esophagus up to the patient's mouth, where it will be maneuvered.

A positioning wire 60 can be threaded between the two opposite holes 24 on the front end locking ring recess 20 and secured in place with an adhesive material. After the locking ring 18 on the front end 16 is attached to the expandable sleeve 30, the positioning wire 60 can be inserted through the holes 24. Preferably, the positioning wire 60 is only attached to the sleeve 12 and not to the front locking ring 18. This allows the locking ring 18 to be removable. Forceps can be used to grab the positioning wire 60 in order to maintain the position of the system 10 on the endoscope tip, to push the system 10 off of the endoscope tip, and to maneuver the system 10 inside the esophagus.

An inflation tube 32 is employed to introduce air into the expandable sleeve 30 during adhering of the bandage to the esophagus. The inflation tube 32 can be formed of a polymeric material such as either polyethylene or a silicon material. A segment of the inflation tube 32 can be threaded through the inflation hole 22 from the center of the sleeve 12. An adhesive can be used to secure the segment of the inflation tube 32 to the outer surface of the sleeve 12. The inflation tube 32 preferably extends the length of the endoscope through the center channel of the endoscope. Once through the endoscope, the tube 32 is joined to a Lure-Lock connector (not shown), which connects the tube 32 with a syringe (not shown). The syringe can be used to inflate the expandable sleeve 30 and deploy the bandage.

The expandable sleeve 30 is preferably a hollow substantially cylindrical component comprising a body portion 34 and a neck portion 36 at each end of the body portion. The expandable sleeve 30 is preferably designed so that the body portion 34 assumes an extended tubular shape while the neck portions 36 maintain a uniform ID cylindrical shape. The expandable sleeve 30 can be slid over the sleeve 12, with the neck portions 36 lining up with the locking ring recess 20. The locking rings 18, 18' fit tightly over the locking ring recesses 20, securing the neck portions 36 of the expandable sleeve 30. The expandable sleeve 30 can be inflated using a syringe attached to the inflation tube 32. The bandage is attached to the outside of the expandable sleeve 30 as shown in FIG. 3. A doctor can maneuver the bandage into position using the system 10, and then inflate the expandable sleeve 30 to a diameter slightly larger than the esophagus when it's relaxed.

Sheath 70 is preferably a thin-walled, cylindrical polyester heat-shrink tubing, typically with a substantially constant ID. The sheath 70 is slid over the expandable sleeve 30 such that the front end is aligned with the front end of the system 10 (see FIG. 4).

The front end of the sheath 70 is secured and sealed with a sheath-securing flap 72 onto the system 10. The system, including the attached sheath 70, is fit onto the tip of the endoscope. The back end of the sheath is secured and sealed with surgical tape onto the endoscope. With both ends secured, the bandage is enclosed in a substantially watertight environment. Besides protecting the bandage, a sheath can ideally push off the bandage from the endoscope to the wound. The inner lips from sheath will push against the bandage. Then, once the bandage is dislodged from the endoscope, the sheath will retract to expose the bandage.

The extended expandable sleeve neck 36 on the back end of the sleeve 12 is used to hold the bandage 50 in the same manner that the sheath-securing flap 72 holds the sheath 70 (see FIG. 3). The extended neck is rolled back and over the edge of the bandage. The elastic properties and the texture of the silicon neck secure the bandage with a fair amount of pressure. As a result, the bandage does not easily slip off of the system 50 while the system pushes through the sheath 70 and off of the endoscope towards the treatment area. However, when the expandable sleeve 30 is inflated to deploy the bandage 50, enough pressure is applied such that the bandage-securing flap 52 loses its grip on the bandage and the bandage is deployed.

The extended expandable sleeve neck 36 on the front end of the expandable sleeve 30 is used to hold the sheath 70, which is needed to keep the bandage dry as the system travels down the esophagus. The extended neck is rolled back and over the end of the sheath as one would roll up the bottom of one's pants. Stretching the expandable sleeve neck over the sheath seals the end of the sheath from water entry. The elastic properties and the texture of the silicon neck secures the sheath with enough pressure so that the sheath does not easily slip off of the system. Forceps can be used to push on the wire with enough force. When this occurs, the sheath-securing flap loses its grip on the sheath. The system slides off the endoscope while the sheath remains secured to the endoscope with surgical tape.

When assembling, the inflation tube and the positioning wire are threaded through their respective holes and permanently secured to the tube with an adhesive. The expandable sleeve is then slid over the tube and enclosing the adhered inflation tube segment in the expandable sleeve's body volume. Finally, the locking rings are fitted over expandable sleeve necks on the locking ring recesses, securing the expandable sleeve and forming an airtight space between the expandable sleeve's body and the outer surface of the tube.

Before operation of the system, the bandage and sheath must be added. The pre-rolled bandage wraps around the system and is secured by rolling the excess flaps of the expandable sleeve overtop of the bandage. To protect the bandage from the wet environment of the esophagus, the sheath, which is described above, and which is preferably made of a polymeric material such as a polyester, slides around the system outside of the bandage and is also secured to the system with the front flap of the expandable sleeve.

The system, along with the bandage and sheath, is now ready to be loaded onto the endoscope. First, the expandable tubing is threaded backwards up the channel of the endoscope from the tip toward the doctor's end using the grasping forceps. Once the inflation tube runs up the channel, the syringe attaches to the inflation tube using tubing connectors. Before fixing the back end of the sheath to the endoscope, the system is positioned around the endoscope such that the positioning wire is within grasp of the forceps. Throughout the operation, the forceps control and hold the system by gripping the positioning wire.

Once the system is integrated with the endoscope, the operation can begin. The endoscope with the system attached is navigated down the esophagus until it reaches the wound. The endoscope will be positioned such that the wound is within view. The system is pushed forward with the forceps until it is released from the sheath and reaches the site. The force of the forceps overcomes the sealing power of the expandable sleeve flaps. The back end of the sheath remains fixed and keeps the sheath in place in order to expose the bandage. Next, the expandable sleeve is inflated with air from the syringe. The flaps of the expandable sleeve roll back off of the bandage as the expandable sleeve inflates to fully expose the bandage to wound. Most importantly, the inflation of the expandable sleeve applies pressure to the bandage against the esophagus. The expandable sleeve must maintain pressure on the bandage to ensure adequate adherence of the bandage to the esophagus. Then, the expandable sleeve is deflated, and the system is retracted from the treatment site back onto the end of the endoscope using the forceps. The performance of the system and bandage can be viewed with the monitor, which is attached to the endoscope's internal imaging equipment. After deployment, the resulting bandage can be examined to check for adherence and accuracy of deployment.

Ex Vivo Testing

The subject system's ability to successfully deploy a bandage was tested on an excised esophagus.

The excised esophagus from a 450 lb. pig was attached to a metal ring using clips. This ring was then secured onto a ring stand, and the esophagus was suspended to its full length. The system of the subject invention was loaded onto the endoscope. Next, the system was inserted into the excised esophagus from the proximal end, and pushed down to the approximate center of the esophagus using the endoscope. The system was deployed and the expandable sleeve was left inflated for about 3 minutes to allow for sufficient adherence of a chitosan bandage to the esophagus. The expandable sleeve was then deflated, and the system was pulled out of the esophagus using the endoscope and forceps.

The esophagus was detached from the stand apparatus, and then cut with scissors vertically down its entire length. The bandage was pulled on using forceps in order to assess the degree of adherence to the esophagus.

The sheath functioned successfully. It provided the bandage with appropriate protection from moisture. This was determined based on the fact that the bandage did not adhere to the sheath—an event that would have occurred had the bandage become wet while the sheath was still covering it.

The expandable sleeve functioned with success according to the defined criterion. It was inflated with 20 ml of air, and, based on observation of the outer profile of the esophagus, it retained this volume of air throughout the 3-minute inflation period.

The bandage adhered tightly to the esophageal lumen. The bandage deployed in a uniform manner and covered the entire inner circumference of the esophagus. When the bandage was pulled on with forceps, it took the entire weight of the excised esophagus to begin separating the bandage from the tissue.

In Vivo Testing

The subject system's ability to successfully deploy a bandage in vivo was tested in several live swine.

A gastroenterologist and selected medical staff conducted the procedures. The system was loaded on to the end of an endoscope. The pig was anesthetized to the point of unconsciousness. The pig was incubated, and monitored closely by qualified animal care professionals. The gastroenterologist inserted the endoscope with the system into the pig via its mouth. When the testing site was reached, the system was deployed, and a chitosan bandage was attached to the pig's esophagus.

After the bandage was deployed, and the system was pulled from within the animal, the entire system (including the sheath) was removed from the endoscope so that the site of bandage application could be investigated with the endoscope alone. After thorough video observation, the endoscope was used to gently push on the bandage to test for proper adherence. Additionally, the endoscope was pushed past the bandage to test whether food could still pass through the center hole.

For one of the trials, the system was testing bleeding lacerations in the esophagus. The pig was heparinized to inhibit its natural clotting abilities so that all clotting observed would be due to the presence of the bandage. Next, the esophageal lumen was lacerated using an endoscopic needle system to the point of bleeding. The system was then used to deploy a bandage in the same manner as previously described such that it covered the bleeding wounds.

A bandage was deployed as described at the gastroduodenal junction. Then, a bandage was deployed at the gastroesophageal junction. Both bandage deployments (at the gastroesophageal junction and the gastroduodenal junction) met all of the criteria and were considered successes.

No adverse consequences were observed as a consequence of delivering the dressing or dressing deployment.

A biopsy forceps was introduced and grabbed the adhered dressing to determine the strength of adhesion. The bonding was strong enough to allow pulling the stomach through the diaphragm, indicating a very strong adhesion of the chitosan dressing to the esophagus Based on both the ex vivo and the in vivo testing results, it was concluded that the system of the present invention could accurately and consistently apply bandages rapidly and safely to tissues in the esophagus and in the duodenum using conventional endoscopes and endoscopic techniques.

The invention claimed is:

1. A method for controlling bleeding and promoting hemostasis within a hollow body organ of a gastrointestinal tract selected from one of an esophagus, a stomach, a duodenum, a small intestine, and a large intestine comprising:
    identifying within the hollow body organ, a tissue treatment region requiring bleeding control with a layered bandage application system comprising a tubular bandage structure, a hollow substantially cylindrical expandable body, and a sleeve;
    providing the tubular bandage structure having a normal interior diameter, the tubular bandage structure comprising a chitosan material, the tubular bandage structure being sized and configured to radially enlarge beyond the normal interior diameter in response to application of radial expansion force;
    providing the hollow substantially cylindrical expandable body sized and configured to expand between a collapsed condition having a first diameter approximating the normal interior diameter and an expanded condition having a second diameter greater than the first diameter;
    providing the sleeve;
    providing the bandage application system in conjunction with a detachable endoscopic device;
    sliding the sleeve over the endoscopic device so as to allow viewing capability from the endoscopic device tip;
    sliding the hollow substantially cylindrical expandable body over the sleeve in the collapsed condition;
    forming the bandage application system by mounting the tubular bandage structure on the hollow substantially cylindrical expandable body;
    introducing the bandage application system and the endoscopic device into the hollow body organ;
    applying radial expansion force to the tubular bandage structure by expanding the hollow substantially cylindrical expandable body from the collapsed condition to the expanded condition to radially enlarge and press the tubular bandage structure within the hollow body organ against all sides of the entire inner circumference of one of the esophagus, the stomach, the duodenum, the small intestine, and the large intestine that includes the tissue treatment region;
    maintaining the hollow substantially cylindrical expandable body in the expanded condition for a period of time sufficient to exert pressure on the radially enlarged tubular bandage structure to adhere the radially enlarged tubular bandage structure to all sides of the entire inner circumference of one of the esophagus, the stomach, the duodenum, the small intestine, and the large intestine that includes the tissue treatment region, whereby bleeding of the tissue will be controlled by sealing the tissue treatment region and creating an active clotting surface;

releasing the radial expansion force by collapsing the hollow substantially cylindrical expandable body from the expanded condition to the collapsed condition; and removing the hollow substantially cylindrical expandable body from the hollow body organ without displacing the adhered and radially enlarged tubular bandage structure;

wherein the radially enlarged tubular bandage structure defines a center hole through which food can pass through the gastrointestinal tract.

2. The method according to claim 1, wherein the bandage application system is introduced under video guidance.

3. The method according to claim 1, wherein the bandage application system is introduced under fluoroscopic control.

4. The method according to claim 1, wherein the hollow substantially cylindrical expandable body is expanded using a gas or fluid.

5. The method according to claim 1, further including providing a protective barrier on the bandage application system so that the tubular bandage structure does not adhere to the bandage application system or to tissue en route to the tissue treatment region.

6. The method according to claim 1, further including providing an outer sheath on the bandage application system to protect the tubular bandage structure from wetness within the hollow body organ.

7. The method according to claim 1, wherein the tubular bandage structure is processed through the digestive system.

8. The method according to claim 1, wherein the hollow substantially cylindrical expandable body is maintained in the expanded condition for about two to five minutes.

9. The method of according to claim 1, further including repeating the method and applying an additional bandage.

10. The method of according to claim 1, wherein the sleeve consists of a polymeric material.

11. The method of according to claim 1, wherein the hollow substantially cylindrical expandable body is an expandable sleeve.

12. The method of according to claim 1, further including at least one locking ring fitted over an end of the sleeve.

13. The method of according to claim 1, further including the step of pushing the bandage application system off of the endoscopic device before applying radial expansion force to the tubular bandage structure.

14. A method for controlling bleeding within a hollow body organ of a gastrointestinal tract selected from one of an esophagus, a stomach, a duodenum, a small intestine, and a large intestine comprising:

identifying within the hollow body organ, a tissue treatment region requiring bleeding control with a bandage application system comprising a sleeve suitable for sliding over an endoscopic device, a hollow expandable body surrounding the sleeve, and a tubular bandage structure surrounding the hollow expandable body;

providing the endoscopic device;

preparing the bandage application system by sliding the sleeve over the endoscopic device;

mounting the hollow expandable body onto the sleeve;

mounting the tubular bandage structure onto the hollow expandable body;

introducing the bandage application system into the hollow body organ;

pushing the bandage application system off of the endoscopic device before adhering the tubular bandage structure to the tissue treatment region;

adhering the tubular bandage structure to the tissue treatment region by expanding the hollow expandable body to radially enlarge and press the tubular bandage structure against all sides of the entire inner circumference of one of the esophagus, the stomach, the duodenum, the small intestine, and the large intestine that includes the tissue treatment region;

sealing the tissue treatment region by adhering the tubular bandage structure, whereby bleeding of the tissue will be controlled;

collapsing the hollow expandable body from the expanded condition to a collapsed condition; and removing the bandage application system from the hollow body organ without displacing the tubular bandage structure;

wherein the radially enlarged tubular bandage structure defines a center hole through which food can pass through the gastrointestinal tract.

15. The method according to claim 14, further including maintaining the hollow expandable body in the expanded condition for a period of time sufficient to adhere the radially enlarged tubular bandage structure.

16. The method according to claim 15, wherein the hollow expandable body is maintained in the expanded condition for about two to five minutes.

17. The method according to claim 14, wherein the bandage application system is introduced under video guidance.

18. The method according to claim 14, wherein the bandage application system is introduced under fluoroscopic control.

19. The method according to claim 14, wherein the hollow expandable body is expanded using a gas or fluid.

20. The method according to claim 14, wherein the hollow expandable body is substantially cylindrical.

21. The method according to claim 14, further including providing a protective barrier on the bandage application system so that the tubular bandage structure does not adhere to the bandage application system or to tissue en route to the tissue treatment region.

22. The method according to claim 14, further including providing an outer sheath on the bandage application system to protect the tubular bandage structure from moisture.

23. The method according to claim 14, wherein the tubular bandage structure is processed through the digestive system.

24. The method of according to claim 14, further including repeating the method and applying an additional bandage.

25. The method of according to claim 14, wherein the sleeve consists of a polymeric material.

26. The method of according to claim 14, wherein the hollow expandable body is an expandable sleeve.

27. The method of according to claim 14, further including at least one locking ring fitted over an end of the sleeve.

28. The method of according to claim 14, wherein the step of sliding the sleeve over the endoscopic device allows viewing capability from the endoscopic device tip.

* * * * *